United States Patent
DeBernardi

(10) Patent No.: US 6,852,335 B2
(45) Date of Patent: Feb. 8, 2005

(54) FOLIC ACID IN SOLID DOSAGE FORMS

(75) Inventor: Douglas P. DeBernardi, Hayward, CA (US)

(73) Assignee: Shaklee Corporation, Pleasanton, CA (US)

( * ) Notice: Subject to any disclaimer, the term of this patent is extended or adjusted under 35 U.S.C. 154(b) by 372 days.

(21) Appl. No.: 10/164,292

(22) Filed: Jun. 5, 2002

(65) Prior Publication Data

US 2003/0017205 A1 Jan. 23, 2003

Related U.S. Application Data

(63) Continuation of application No. 09/614,799, filed on Jul. 12, 2000, now Pat. No. 6,465,013
(60) Provisional application No. 60/143,385, filed on Jul. 12, 1999.

(51) Int. Cl.$^7$ .................... A61K 31/4985; A61K 9/28
(52) U.S. Cl. .................... 424/480; 424/474; 427/2.14
(58) Field of Search ................ 424/480, 474, 424/479, 481; 427/2.14; 514/904, 960

(56) References Cited

U.S. PATENT DOCUMENTS

| | | | |
|---|---|---|---|
| 5,368,861 A | 11/1994 | Ushimaru et al. |
| 5,462,754 A | 10/1995 | Synosky et al. |
| 5,569,477 A | 10/1996 | Nesbitt |
| 5,686,133 A | 11/1997 | Amidon et al. |
| 5,834,022 A | 11/1998 | Amidon et al. |
| 5,849,338 A | 12/1998 | Richardson et al. |
| 5,851,275 A | 12/1998 | Amidon et al. |
| 5,855,914 A | 1/1999 | Koyama et al. |
| 6,261,600 B1 | 7/2001 | Kirschner et al. |

OTHER PUBLICATIONS

Porter, Stuart C., "Coating of Pharmaceutical Dosage Forms," Pharmaceutical Sciences, Chapter 90, pp. 1666–1675, Mack Publishing Company, 1990.

*Primary Examiner*—Edward J. Webman
(74) *Attorney, Agent, or Firm*—Klarquist Sparkman, LLP

(57) ABSTRACT

A nutritional tablet or caplet has a film coating that contains folic acid available for rapid release upon contact with gastric fluid. The film coating also includes a film forming polymer such as hydroxypropyl methylcellulose.

13 Claims, No Drawings

FOLIC ACID IN SOLID DOSAGE FORMS

This is a continuation of Application No. 09/614,799, filed Jul. 12, 2000, now U.S. Pat. No. 6,465,013, which claims the benefit of U.S. Provisional Application No. 60/143,385, filed Jul. 12, 1999, the contents of both of which are incorporated herein by reference.

BACKGROUND AND SUMMARY OF THE INVENTION

This invention relates to folic acid provided in solid dosage forms. Folic acid (folate) is a water-soluble B vitamin that is widely distributed in foods. In the body, folates function as coenzymes in amino acid metabolism and nucleic acid synthesis. Folate deficiencies lead to impaired cell division and altered protein synthesis.

The physiological benefits of folic acid consumption are numerous. Newborn children of women receiving adequate folic acid in their diet show a lower incidence of spina bifida and anencephaly, both of which are neural tube defects affecting approximately 2500 newborns annually. Adequate intake of folic acid reduces homocysteine levels in the blood, significantly reducing the risk, particularly in men, of heart attack, stroke and peripheral vascular disease. Women with a high intake of folic acid have been shown to be at much reduced risk of developing colorectal adenomas.

The U.S. Public Health Service recommends that women of childbearing age ingest 400 mcg of folic acid per day to reduce their risk of having a child with neural tube defects. The need for women of childbearing age to obtain adequate daily intakes of folic acid, prompted the U.S. Food and Drug Administration (FDA) to issue rules that require fortification of enriched grain products with folic acid. The U.S. Public Health Service also recommends that women obtain folic acid by consuming dietary supplements, such as multivitamin or Vitamin B Complex products.

Dietary sources of folic acid include liver, leafy dark green vegetables, legumes, citrus fruits and juices, and most berries. However, studies indicate that folic acid, in its pure form, is significantly more bioavailable than naturally occurring folate. Approximately three-fourths of the foliate in a typical U.S. diet is present as polyglutamate, a form shown to be about half as bioavailable as crystalline folic acid.

Folic acid is recognized as a significant source of folic acid for a large segment of the population, but recent studies indicate that a number of commercially available dietary supplements do not meet the minimum folic acid dissolution requirements of the USP (U.S. Pharmacopeia). Hoag et al. found that 67% of the folic acid-containing prescription prenatal products tested failed to meet the USP dissolution standard (75% of the labeled amount of folic acid must dissolve in one hour in 900 ml of water at 37° C.) in effect at the time of their research. (Hoag, S W, Ramachandruni H, Shangraw R F., "Failure of prescription prenatal vitamin products to meet USP standards for folic acid dissolution", J. Am. Pharm. Assoc. 1997; NS37; 397–400).

The FDA has expressed concern over the Hoag study and has also tested a small number of folic acid-containing dietary supplements. They found that some were sub-potent and failed to meet the dissolution standard as well. While no fundamental scientific studies have been conducted to understand the mechanism of folic acid dissolution in dietary supplements, Hoag et al. postulate that raw material properties, manufacturing methods, assay methodologies, and dissolution methodologies might play roles in the poor dissolution performance of certain folic acid containing dietary supplements.

Recently, industry has focused on the dissolution medium as a possible limiting factor in the dissolution test. Folic acid has very limited-solubility in water, approximately 1.6 mcg/ml at 25° C. (The Merck Index, 12$^{th}$ edition). This equates to a solubility limit of about 800 mcg of folic acid in the 900 ml of water that is specified as the dissolution medium for the test. Since the test is performed at 37° C., the actual solubility limit is somewhat higher, but is still only 3–4 times the amount of folic acid contained in most single tablet dosages (200–800 mcg folic acid per tablet). The CRN (Council for Responsible Nutrition), an association of the dietary supplements industry, initiated a study of an alternative dissolution medium, 0.05M citrate buffer. Citrate buffer significantly improved the folic acid dissolution performance of dietary supplements that performed poorly in water. However, for certain products the improvement was not sufficient to consistently meet the USP requirement of greater than 75% of the labeled amount of folic acid dissolved in one hour. Regardless, based on the results of this study, the USP has proposed adopting the 0.05M (pH=6.0) citrate buffer dissolution medium.

While progress has been made on the test methodology side, there is still no guarantee that any individual product formulation will display acceptable folic acid dissolution. In most conventional tablet formulations, folic acid is preblended with other tablet excipients prior to tablet formation to insure uniformity of dosage due to the low level of use ($\leq$400 mcg/dose). Insoluble carriers such as dibasic calcium phosphate are often used in multi-vitamin, multi-mineral formulations as both calcium and phosphorus sources. These materials are resistant to aqueous dissolution and may result in a physical shielding of folic acid from the dissolution medium during the test. It has been hypothesized that folic acid may complex with minerals such as $Fe^{+2}$, $Cu^{+2}$ and $Zn^{+2}$, affecting folic acid solubility.

What is needed is a simple, effective and consistent way to improve the folic acid dissolution performance of dietary supplements in order to enhance the bioavailability of folic acid to the human body. The process described herein produces dietary supplements having significantly improved folio acid dissolution performance. Using that process it is possible to produce dietary supplement solid dosage forms (tablets) from which folic acid dissolves more rapidly than heretofore was possible. With this process one can readily produce a folic acid dosage form from which essentially 100% of the labeled amount of folic acid can dissolve within the time frame of the USP dissolution test (one hour).

In aqueous solutions, folic acid is known to have very limited water solubility and poor chemical stability. In the current process, this limited aqueous solubility is turned into an advantage. Crystalline folic acid can be formulated in combination with common aqueous film coating agents such hydroxypropyl methylcellulose, acacia gum, maltodextrin, soluble starches and pullulan (a naturally occurring polysaccharide derived from *Aureobasidium Pullulans* yeast). In these formulations, the folic acid concentration is significantly above its aqueous solubility limit and the folic acid is present predominantly as a dispersed solid. In this dispersed state, the folic acid may then be applied by conventional aqueous film coating methods to the outside surface of dietary supplement tablets or caplets so as to form a uniform folic acid containing coating. Folic acid in such an outer coating is released more rapidly than when folic acid is contained in the core tablet, resulting in increased bioavailability.

DETAILED DESCRIPTION

According to the present invention, a dietary supplement dosage form includes folic acid in a coating layer over the surface of a tablet or caplet that contains other nutrients or active ingredients. The coating layer is formed by providing an aqueous liquid that contains a film forming polymer and disbursed folic acid, coating the liquid onto substrate tablets or caplets, and then drying to fix the coating. The film coating is formed on at least a portion, preferably on all, of the exposed surface of a core containing other nutrients and/or pharmaceutical actives.

The film forming agent is typically a water soluble film forming polymer, such as hydroxypropyl methylcellulose, methylcellulose, ethylcellulose, hydroxypropyl cellulose, povidone, polydextrose, lactose, maltodextrin, acrylic polymer, acacia gum, soluble starches, pullulan (a naturally occurring polysaccharide derived from *Aureobasidium Pullulans* yeast), and mixtures thereof.

The aqueous coating liquid may optionally contain a plasticizer, such as hydroxylated soy lecithin, castor oil, polyethylene glycol, propylene glycol or glycerine, and a coloring or opacifying agent. Folic acid is a yellow crystalline solid so the resulting film coating is imparted with a yellow color unless modified by the addition of appropriate natural or synthetic coloring agents. The film coating may also contain a flavoring and/or sweetening agent to improve palatability.

The folic acid may be any pharmaceutically acceptable crystalline folic acid, such as USP Folic Acid manufactured by Takeda Chemical Industries, Ltd.

Suitable dispersions will generally contain (w/w) about 8% to about 15% of the film forming polymer, about 0.05% to about 0.35% of the folic acid, and about 80% to about 90% purified water. Good results are achieved with a dispersion containing (w/w) about 10% to about 15% of the film forming polymer, about 0.20% to about 0.35% of the folic acid, and about 80% to about 90% purified water. A particularly useful aqueous film coating formulation is composed of about 10 to 11% by weight hydroxypropyl methylcellulose, about 0.35% by weight hydroxylated soy lecithin, and about 0.25% by weight of the folic acid, in water to produce an aqueous dispersion. Equivalents for these compounds, other than the folic acid, as are well known in the tablet coating art, may be used in approximately the same proportions.

The film coating dispersion can be made by hydrating the water soluble film-forming polymer and diluting to the suitable viscosity for coating the tablet cores. The required quantity of the folic acid is disbursed in a separate aliquot of water. The folic acid should be dispersed in water before being added to the other ingredients.

The dispersion is applied to tablet or caplet cores containing one or more other nutrients and/or medicaments. The cores are prepared in accordance with standard pharmaceutical tableting techniques, including wet-granulation, dry-granulation, direct compression, spheronization and the like. The dispersion is applied to the cores using conventional pharmaceutical coating equipment, such as the LabCoat II film coating pan manufactured by O'Hara Manufacturing Limited of Toronto, Canada. Other film coating techniques suitable for use in the present invention are described in *Remington's Pharmaceutical Sciences* (edited by A. L. Gennaro), Mack Publishing Co., Easton, Pa., 18th ed., Chapter 90 (1990), which is hereby incorporated by reference. The preferred method for applying the film coatings of the present invention is aqueous film coating using conventional coating equipment but fluid-bed or Wurster coating methods may also be employed.

The dried film coating generally constitutes from about 1.0% to 3.0%, preferably about 2.0% to 2.5% by weight of the total weight of the solid dosage form and is about 0.10 to 0.20 mm thick. It will be appreciated that the thickness of the coating can be varied as necessary to adjust the size of the folic acid dose to be provided in the coating. To provide the earliest release of folic acid, the film coating portion of the dosage form should be located outside all portions that contain other nutrients. A protective coating layer could be provided over the coating that contains the folic acid, but this is not necessary.

When film-coated tablets or caplets of the present invention are administered, the tablet or caplet contacts the gastric acid of the stomach, which immediately starts to break down the film coating, and thereby promptly releases folic acid. The gastric fluid takes longer to disintegrate the tablet core. Thus, tablets or caplets prepared in accord with the present invention release a folic acid dose more rapidly than conventional tablets or caplets wherein folic acid is present with the other nutrients and/or active ingredients in the tablet core.

The film coating technique of the present invention results in a very consistent delivery of a folic acid dosage since very uniform solution compositions can be achieved. The described process can be used to significantly improve the folic acid dissolution performance and folic acid bioavailability for any tablet formulation that is compatible with an aqueous film coating process. Tablets or caplets manufactured according to the invention can be formed to meet a variety of standards and, in particular, can have a film coating from which at least about 75% of the folic acid dissolves in one hour in 900 ml of water or 0.05M citrate buffer at 37° C.

It is common industry practice to include an overage of folic acid in tablet or caplet formulations, which must meet a minimum of 100% of their labeled potency throughout their shelf life. This is done to allow for variations in the manufacturing process as well as losses due to folic acid instability. Typically folic acid overages range from about 10 to 40%. This means that the "75%" folic acid dissolution standard typically is met when a tablet or caplet produced according to the present invention has a film coating from which as little as 50% of the total amount of folic acid actually present dissolves in one hour in 900 ml of water or 0.05M citrate buffer at 37° C.

A specific embodiment of the present invention is illustrated by way of the following example. This invention is not confined to the specific limitations set forth in the example, but rather to the scope of the appended claims. Unless otherwise stated, the percentages and ratios given below are by weight.

EXAMPLE

A dispersion of folic acid is prepared by pre-dispersing crystalline folic acid in purified water. The resulting folic acid slurry is then added to a hydroxypropyl methylcellulose dispersion that has been properly prepared so that the polymer is completely hydrated. Hydroxylated soy lecithin is then added. The combined ingredients are then mixed for 20 to 30 minutes. Adding the folic acid to a separate aliquot of purified water is the preferred way to consistently wet and disperse the crystalline solid. After mixing, the dispersion should then be allowed to deaerate for 2 to 4 hours. The result is a folic acid dispersion having the ingredient ratio shown in Table I:

TABLE I

| Component | Approximate Formula (% w/w) |
| --- | --- |
| Hydroxypropyl methylcellulose | 10.17 |
| Hydroxylated soy lecithin | 0.35 |
| Folic acid | 0.25 |
| Purified water | 89.23 |

The dispersion can then be atomized and sprayed onto the surface of dietary supplement cores using appropriate conditions to form a uniform coating.

Film coating was performed in an O'Hara Manufacturing Limited 24" perforated coating pan using standard coating procedures. Two spray guns were employed with each gun delivering approximately 20 grams/minutes of film coating dispersion to a coater tablet load of approximately 10 kg. Inlet air temperatures of 60° C. to 70° C. were employed to maintain an,outlet air temperature of approximately 41° C. to 44° C. during the coating process. After the appropriate weight gain of the tablets was achieved, the tablets were cooled to 30° C. and discharged.

Folic acid dissolution performance was evaluated for the folic acid coated tablets and traditional B-vitamin tablets containing crystalline folic acid in a direct compression tablet matrix consisting primarily of dicalcium phosphate. Folic acid dissolution was determined on the resulting tablets using the USP dissolution procedure prescribed for nutritional supplements containing folic acid. (USP23 as modified by the USP23 Supplements and the *U.S. Pharmacopeial Forum*, Vol. 25, Number 3, May–June 1999, pp. 8283–8284, all of which publications are incorporated herein by reference.)

The results set forth in Table II demonstrate that the coated tablets made folic acid available more rapidly than the tablets having folic acid integrated with the other nutrients.

TABLE II

| | % of labeled amount of folic acid dissolved in 1 hour (n = 3) |
| --- | --- |
| Folic acid in tablet core | 30.7% (25.6%*) |
| Folio acid in tablet coating | 102.0% (72.9%*) |

900 ml 0.05M citrate buffer, Apparatus 2, 75 rpm paddle, 37° C.
(*as percent of assayed amount)

As can be seen from Table II, the tablet having folic acid in a film coating had at least 75% of the labeled amount of folic acid dissolve in one hour in 900 ml of 0.05M citrate buffer at 37° C., representing a significant enhancement in bioavailability over tablets containing folic acid within the core tablet matrix.

Although the principles of the present invention are described with reference to a preferred embodiment, it should be apparent to those of ordinary skill in the art that the details of the embodiment may be modified without departing from such principles. The present invention includes all modifications, variations, and equivalents thereof as fall within the true scope and spirit of the following claims.

What is claimed is:

1. A method for preparing a film coated nutritional tablet or caplet comprising:

preparing an aqueous dispersion consisting essentially of a film forming polymer and folic acid;

coating a substrate tablet or caplet that contains at least one nutrient or active ingredient other than folic acid with the aqueous dispersion; and drying the dispersion to form a tablet or caplet that is at least partially covered by a film coating that comprises folic acid.

2. The method of claim 1 wherein the film forming polymer is hydroxypropylmethylcellulose.

3. The method of claim 1 wherein the aqueous dispersion contains hydroxylated soy lecithin as a natural plasticizer.

4. The method of claim 1 wherein the aqueous dispersion comprises (w/w) about 8 to about 15 percent hydroxypropyl methylcellulose film forming polymer, about 0.05 to about 0.35 percent folic acid, and about 80 to about 90 percent purified water.

5. The method of claim 4 wherein the dispersion further contains a plasticizer.

6. The method of claim 5 wherein the plasticizer is of the group consisting of hydroxylated soy lecithin, castor oil, polyethylene glycol, propylene glycol, glycerine, and mixtures thereof.

7. The method of claim 1 wherein the aqueous dispersion comprises (w/w) about 10 to about 15 percent hydroxypropyl methylcellulose film forming polymer, about 0.20 to about 0.35 percent folic acid, and about 80 to about 90 percent purified water.

8. The method of claim 7 wherein the dispersion further contains a plasticizer.

9. The method of claim 8 wherein the plasticizer is of the group consisting of hydroxylated soy lecithin, castor oil, polyethylene glycol, propylene glycol, glycerine, and mixtures thereof.

10. The method of claim 1 wherein the aqueous dispersion is prepared and applied such that the resulting tablet or caplet has a film coating from which at least 50% of the folic acid dissolves in one hour in 900 ml of water at 37° C.

11. The method of claim 1 wherein the aqueous dispersion is prepared and applied such that the resulting tablet or caplet has a film coating from which at least 75% of the folic acid dissolves in one hour in 900 ml of water at 37° C.

12. The method of claim 1 wherein the aqueous dispersion is prepared and applied such that the resulting tablet or caplet has a film coating from which at least 50% of the folic acid dissolves in one hour in 900 ml of 0.05M citrate buffer at 37° C.

13. The method of claim 1 wherein the aqueous dispersion is prepared and applied such that the resulting tablet or caplet has a film coating from which at least 75% of the folic acid dissolves in one hour in 900 ml of 0.05M citrate buffer at 37° C.

* * * * *